United States Patent [19]

Likibi et al.

[11] Patent Number: 5,670,685
[45] Date of Patent: Sep. 23, 1997

[54] PROCESS FOR PREPARING CARBOXYLATES OF POLYOXYALKYLENE SILOXANES

[75] Inventors: Parfait J. M. Likibi; Robert V. Casciani; Gregory L. McCraw, all of Charlotte, N.C.

[73] Assignee: Clariant Finance (BVI) Limited, Tortola, Virgin Islands (Br.)

[21] Appl. No.: 471,809

[22] Filed: Jun. 6, 1995

Related U.S. Application Data

[60] Continuation of Ser. No. 268,743, Jun. 30, 1994, Pat. No. 5,504,246, which is a division of Ser. No. 675,220, Mar. 26, 1991, Pat. No. 5,334,756.

[51] Int. Cl.$^6$ ............................................. C07F 7/08
[52] U.S. Cl. ........................................................ 556/437
[58] Field of Search ............................................ 556/437

[56] References Cited

U.S. PATENT DOCUMENTS

| | | |
|---|---|---|
| 2,384,817 | 9/1945 | Chitwood . |
| 2,572,876 | 10/1951 | Rust et al. . |
| 2,770,632 | 11/1956 | Merker . |
| 3,168,543 | 2/1965 | Black et al. . |
| 3,218,344 | 11/1965 | Bailey . |
| 3,219,726 | 11/1965 | Bailey et al. . |
| 3,234,252 | 2/1966 | Pater . |
| 3,402,192 | 9/1968 | Haluska . |
| 3,427,271 | 2/1969 | McKeller . |
| 3,551,382 | 12/1970 | Schnurrbusch et al. . |
| 3,560,544 | 2/1971 | Haluska . |
| 3,637,783 | 1/1972 | Haluska . |
| 3,700,712 | 10/1972 | Ostrozynski . |
| 3,715,377 | 2/1973 | Siciliano . |
| 4,200,724 | 4/1980 | Darms et al. . |
| 4,220,748 | 9/1980 | Hashimoto et al. . |
| 4,223,460 | 9/1980 | Willis et al. . |
| 4,460,712 | 7/1984 | Blizzard et al. . |
| 4,495,340 | 1/1985 | Blizzard et al. . |
| 4,658,049 | 4/1987 | Nakano et al. ........................ 556/437 |
| 4,766,153 | 8/1988 | Casciani . |
| 4,978,785 | 12/1990 | Sanderson et al. . |
| 5,010,173 | 4/1991 | O'Lenick, Jr. et al. . |
| 5,162,579 | 11/1992 | Fried . |
| 5,175,359 | 12/1992 | Fried . |
| 5,175,360 | 12/1992 | Fried . |
| 5,250,727 | 10/1993 | Fried . |

FOREIGN PATENT DOCUMENTS

| | | |
|---|---|---|
| 412378 | 2/1991 | European Pat. Off. . |
| 488467 | 6/1992 | European Pat. Off. . |
| 2208297 | 3/1989 | United Kingdom . |

OTHER PUBLICATIONS

J. Org. Chem., vol. 52, pp. 2559–2562 (1987).
J. Org. Chem., vol. 55, pp. 462–466 (1990).

*Primary Examiner*—Deborah D. Carr
*Attorney, Agent, or Firm*—Robert S. Honor; Carl W. Battle; Joseph J. Borovian

[57] ABSTRACT

A process for preparing carboxylates of polyoxyalkylene siloxanes and -amines, alkylpolyoxyalkylenes, polyoxyalkylene block polymers, alkylamidepolyoxyalkylenes and alkylpolyglucosides comprising subjecting a primary hydroxyl group-containing polyoxyalkylene compound or alkylpolyglucoside to mild oxidation. The invention also relates to the novel polyoxyalkylene amine and alkylamidepolyoxyalkylene carboxylates prepared by the process.

32 Claims, No Drawings

PROCESS FOR PREPARING CARBOXYLATES OF POLYOXYALKYLENE SILOXANES

This is a continuation of application Ser. No. 08/268,743, filed Jun. 30, 1994, now U.S. Pat. No. 5,504,246, which in turn is a division of application Ser. No. 07/675,220, filed Mar. 26, 1991, now U.S. Pat. No. 5,334,756.

The present invention relates to an improved process for preparing carboxylates of polyoxyalkylene siloxanes and -amines, alkylpolyoxyalkylenes, polyoxyalkylene block polymers, alkylamidepolyoxyalkylenes and alkylpolyglucosides comprising subjecting a primary hydroxyl group-containing polyoxyalkylene siloxane or amine, alkylpolyoxyalkylene, polyoxyalkylene block polymer, alkylamidepolyoxyalkylene or alkylpolyglucoside to mild oxidation. The invention also relates to certain of the carboxylates prepared by the improved process as novel compounds.

BACKGROUND OF THE INVENTION

Over the last 50 years, numerous polyoxyalkylene containing surfactants and specialty chemicals have been developed for commercial application (see for example Shick, M. J., *Nonionic Surfactants,* 1967, Marcel Dekker). These materials, in general, have broad utility as emulsifiers, dispersants, lubricants, detergents, antistats, solubilizers, or thickeners in such industries as cosmetic/personal care, household products, textile, paper, I & I, coatings, and resource recovery.

More specifically, silicone containing surfactants are taking on greater importance in the cosmetic industry. The major class of these compounds is made up of a polydimethylsiloxane backbone to which polyethers have been grafted through a hydrosilation reaction. The other class is made up of an ABA block copolymer of polyoxyalkylene (A) and polydimethylsiloxane (B).

Polyoxyalkylene amines are of great importance in the emulsion polymerization industry and in fiber-related industries where static control is important. Their polyoxyalkylene branches are composed of ethylene oxide polymers or block copolymers of propylene oxide and ethylene oxide.

Moreover, alkylpolyoxyalkylenes, polyoxyalkylene block polymers, alkylamidepolyoxyalkylenes and alkylpolyglucosides are of great importance in the detergent industry.

Potentially, all of the above mentioned compounds could be converted to the corresponding carboxylated derivatives. However, only the alkyl- and arylpolyoxyalkylene carboxylates have been commercialized (via the Williamson ether synthesis). These products have enjoyed relative success in such areas as cosmetic/personal care, household products, agricultural formulations, and the like. Accordingly, in view of their apparent usefulness in a variety of applications, a number of research endeavors have been directed to developing a simple, yet selective process for preparing carboxylates of polyoxyalkylene siloxanes and -amines, alkylpolyoxyalkylenes, polyoxyalkylene block polymers, alkylamidepolyoxyalkylenes and alkylpolyglucosides, without appreciable success.

Although many suitable processes are known for preparing the corresponding carboxylates of these materials, none are free of certain disadvantages which make them rather impractical from a commercial standpoint. For example, although polyoxyalkylene amine carboxylates may be prepared by the Williamson synthesis, it has been found that this reaction indiscriminately leads to both N and O carboxymethylation which results in the undesired quaternization of nitrogen atoms. In addition, the carboxylation of alkylpolyglucosides by the oxidation of primary alcohol sites over platinum catalysts with oxygen as the oxidizer has been thus far commercially unattractive due to economics. Furthermore, no one process has proven to be broadly applicable to all classes of these polyoxyalkylene adducts.

DESCRIPTION OF THE PRIOR ART

J. Org. Chem., Vol. 52, pgs. 2559-2562 (1987) discloses a two-phase (water/solvent) process for oxidizing primary alcohols to aldehydes or carboxylic acids using oxoammonium salts. In addition to the fact that this process employs a phase-transfer catalyst, the use of a solvent, viz., methylene chloride, presents problems from a production standpoint.

U.S. Pat. No. 4,658,049 discloses certain carboxyl-group containing siloxane compounds exhibiting superior heat stability, which compounds are useful as emulsifying agents and surface modifiers for inorganic materials. The final products are prepared by subjecting a particular ester compound and a particular siloxane compound to hydrosilylation, and subjecting the resultant ester to hydrolysis.

U.S. Pat. No. 3,560,544 discloses certain triorganosiloxy endblocked polyoxyalkylene siloxane polymers which are useful as wetting agents, detergents and emulsifying agents. The final products are prepared by adding a particular organo-silicon compound to any cyclic anhydride of an aliphatic carboxylic acid, heating the admixture and recovering the desired end product.

Although each of the above references discloses a suitable process for preparing the desired end products, there still exists a dire need for a simple, yet selective process for preparing carboxylates of polyoxyalkylene siloxanes and -amines, alkylpolyoxyalkylenes, polyoxyalkylene block polymers, alkylamidepolyoxyalkylenes and alkylpolyglucosides. To this end, the present invention is directed to an improved process for preparing said carboxylates which is quite attractive from a commercial standpoint.

OBJECTS OF THE INVENTION

It is an object of the instant invention to provide an improved process for preparing carboxylates of polyoxyalkylene siloxanes and -amines, alkylpolyoxyalkylenes, polyoxyalkylene block polymers, alkylamidepolyoxyalkylenes and alkylpolyglucosides.

It is another object of the instant invention to provide an improved process for preparing carboxylates of polyoxyalkylene siloxanes and -amines, alkylpolyoxyalkylenes, polyoxyalkylene block polymers, alkylamidepolyoxyalkylenes and alkylpolyglucosides which is simple, yet selective.

It is yet another object of the instant invention to provide an improved process for preparing carboxylates of polyoxyalkylene siloxanes and -amines, alkylpolyoxyalkylenes, polyoxyalkylene block polymers, alkylamidepolyoxyalkylenes and alkylpolyglucosides which is simple, yet selective, practical and economical and thereby quite attractive from a commercial standpoint.

DESCRIPTION OF THE INVENTION

The attainment of the above objects is made possible by the instant invention which involves the mild oxidation of polyoxyalkylene siloxanes and -amines, alkylpolyoxyalkylenes, polyoxyalkylene block polymers, alkylamidepolyoxyalkylenes and alkylpolyglucosides containing primary hydroxyl groups to the corresponding carboxylates. More particularly, the instant process involves reacting one mole of a primary hydroxyl group-containing polyoxyalkylene siloxane or -amine, alkylpolyoxyalkylene, polyoxyalkylene block polymer, alkylamidepolyoxyalkylene or alkylpolyglucoside with at least an equimolar amount of either an inorganic or organic halo-containing oxidizing agent in the presence of a weak base and a catalytic amount of a hindered nitroxide to produce the corresponding carboxylates.

Suitable polyoxyalkylene siloxane carboxylates which may be prepared by the process of the instant invention include the compounds of formula IA:

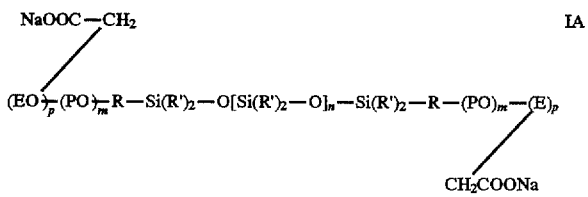

where each R is $C_1$–$C_{20}$alkyl;
each R' is $C_1$–$C_{20}$alkyl, aryl or benzyl;
each m is 0 or an integer 1 to 100;

n is 0 or an integer 1 to 1000;
and each p is an integer 1 to 100.

In the above formula, preferred compounds are those where each R is $C_3$–$C_{10}$alkyl, each R' is $C_1$–$C_6$alkyl or benzyl, each m is 1–10, and n is 0 or an integer 1 to 30. The more preferred compounds of the above formula are those where each R is $C_3$–$C_6$alkyl, each R' is $C_1$–$C_4$alkyl, each m is 0, or an integer 1 or 2, and n is an integer 1 to 8.

Other suitable polyoxyalkylene siloxane carboxylates which may be prepared by the process of the instant invention are the compounds of formula IB:

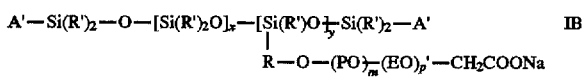

where R, each R' and m are as defined above with regard to the compounds of formula IA;
p' is an integer 1 to 200;
each A' has the same significance as R' defined above or is a group
R—O—(PO)$_m$—(EO)$_{p'}$—CH$_2$COONa,
where R, m and p' are as defined above;
and x+y is 0 or an integer 1 to, 1000.

Of the compounds of formula IB, preferred are the compounds where R is $C_3$–$C_{10}$alkyl, each R is $C_1$–$C_6$alkyl or benzyl, m is 1 to 10, p is 1 to 150, each A is $C_1$–$C_6$alkyl, and x+y is 0 or an integer 1 to 600. The more preferred compounds of formula IB are those where R is $C_3$–$C_6$alkyl, each R is $C_1$–$C_4$alkyl, m is 0 or an integer 1 or 2, p is 1 to 100; each A is $C_1$–$C_4$alkyl, and x+y is an integer 10 to 300.

Suitable polyoxyalkylene amine carboxylates which may be prepared by the process of the instant invention include the compounds of formula IIA:

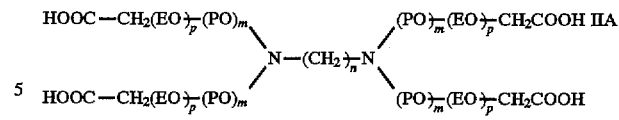

where each m is 0 or an integer 1 to 50;
n is 0 or an integer 1 to 10;
and each p is 0 or an integer 1 to 100.

Of the compounds of formula IIA, preferred compounds are those where each m is 0 or an integer 1 to 30, n is an integer 2 to 6 and each p is 0 or an integer 1 to 80. The more preferred compounds of formula IIA are those where each m is an integer 1 to 25, n is an integer 2 to 4 and each p is an integer 1 to 60.

Other suitable polyoxyalkylene amine carboxylates which may be prepared by the process of the instant invention are the compounds of formula IIB:

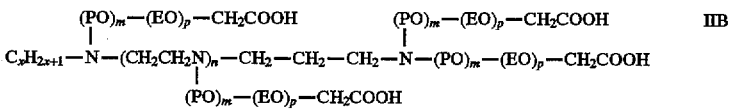

where each m is 0 or an integer 1 to 30;
n is 0 or an integer 1 to 10;
each p is an integer 3 to 30;
and x is an integer 5 to 24.

Of the compounds of formula IIB, preferred compounds are those where each m is 0 or an integer 1 to 10, n is 0 or an integer 1 to 6, each p is an integer 3 to 10, and x is an integer 10 to 20. The more preferred compounds of formula IIB are those where each m is 0 or the sum of the m's is an integer 15 to 25, n is 0 or an integer 1 or 2, the sum of the p+s is an integer 10 to 20, and x is an integer 12 to 18.

Still other suitable polyoxyalkylene amine carboxylates which may be prepared by the process of the instant invention are the compounds of formula IIC:

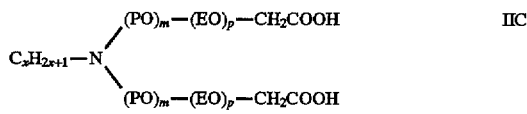

where each m is 0 or an integer 1 to 10;
each p is an integer 3 to 40;
and x is an integer 6 to 24.

Of the compounds of formula IIC, preferred compounds are those where each m is 0 or an integer 1 to 10, each p is an integer 3 to 20, and x is an integer 6 to 18. The more preferred compounds of formula IIC are those where each m is 0 or an integer 1 or 2, the sum of the p+s is an integer 8 to 20, and x is an integer 12 to 18.

Yet still other suitable polyoxyalkylene amine carboxylates which may be prepared by the process of the instant invention are the compounds of formula IID:

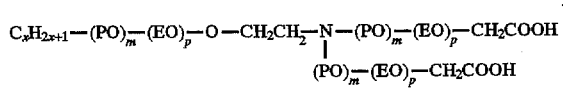    IID where each m is 0 or an integer 1 to 20;

each p is an integer 3 to 40;

and x is an integer 6 to 20.

Of the compounds of formula IID, preferred compounds are those where each m is 0 or an integer 1 to 10, each p is an integer 3 to 20, and x is an integer 10 to 18. The more preferred compounds of formula IID are those where each m is 0 or an integer 1 or 2, each p is an integer 4 to 10, and x is an integer 10 to 14.

Further suitable polyoxyalkylene amine carboxylates which may be prepared by the process of the instant invention are the compounds of formula IIE:

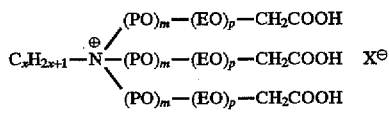 IIE where each m is 0 or an integer 1 to 40;

each p is an integer 3 to 20;

x is an integer 6 to 20;

and $x^{\ominus}$ is an anion.

Of the compounds of formula IIE, preferred compounds are those where each m is 0 or an integer 1 to 20, each p is an integer 3 to 10, x is an integer 10 to 18, and $x^{\ominus}$ is a halide, $C_{1-3}$alkylsulfate or phosphate anion. The more preferred compounds of formula IIE are those where each m is 0, the sum of the p+s is 10, x is an integer 16 to 18 and $x^{\ominus}$ is a phosphate anion.

Still further suitable polyoxyalkylene amine carboxylates which may be prepared by the process of the instant invention are the compounds of formula IIF:

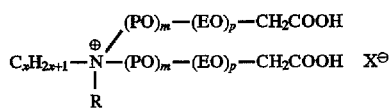 IIF where R is methyl, ethyl or benzyl;

each m is 0 or an integer 1 to 40;

each p is an integer 3 to 20;

and x is an integer 6 to 20;

and $x^{\ominus}$ is an anion.

Of the compounds of formula IIF, preferred compounds are those where R is methyl or ethyl, each m is 0 or an integer 1 to 10, each p is an integer 3 to 10, x is an integer 10 to 18, and $x^{\ominus}$ is a halide, $C_{1-3}$alkylsulfate or phosphate anion. The more preferred compounds of formula IIF are those where R is methyl, each m is 0, the sum of the p+s is 13, x is an integer 12 to 14 and $x^{\ominus}$ is a chloride anion.

Suitable alkylpolyoxyalkylene carboxylates which may be prepared by the process of the instant invention are the compounds of formula III:

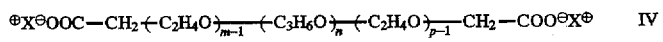    III where R is straight or branched chain $C_4$–$C_{22}$ alkyl, alkenyl or alkylphenyl, or a mixture thereof;

m is 0 or an integer 1 to 50;

n is an integer 1 to 50;

and $x^{\oplus}$ is hydrogen or an alkali metal cation.

In the above formula, preferred compounds are those where R is straight or branched chain $C_4$–$C_{18}$ alkyl, alkenyl or alkylphenyl, or a mixture thereof, m is 0 or an integer 1 to 20, n is an integer 1 to 20, and $x^{\oplus}$ is hydrogen, sodium, potassium or lithium. The more preferred compounds of the above formula are those where R is straight or branched chain $C_{10}$–$C_{18}$ alkyl, alkenyl or alkylphenyl, or a mixture thereof, m is 0 or an integer 1 to 10, n is an integer 1 to 10, and $x^{\oplus}$ is hydrogen, sodium or lithium.

Suitable polyoxyalkylene block polymer carboxylates which may be prepared by the process of the instant invention are the compounds of formula IV:

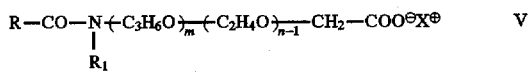 IV where m+p is an integer 1 to 400;

n is 0 or an integer 1 to 200;

and each $x^{\oplus}$ is hydrogen or an alkali metal cation.

In the above formula, preferred compounds are those where m+p is an integer 1 to 200, n is an integer 2 to 100, and each $x^{\oplus}$ is hydrogen, sodium or lithium. The more preferred compounds of the above formula are those where m+p is an integer 2 to 10, n is an integer 10 to 30, and each $x^{\oplus}$ is hydrogen or sodium.

Suitable alkylamidepolyoxyalkylene carboxylates which may be prepared by the process of the instant invention are the compounds of formula V:

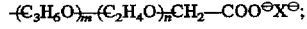 V where R is straight or branched chain $C_4$–$C_{30}$ alkyl or alkenyl, or a mixture thereof;

$R_1$ is H or a moiety

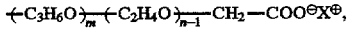;

m is 0 or an integer 1 to 50;

n is an integer 1 to 50;

and $X^{\oplus}$ is hydrogen or an alkali metal cation.

In the above formula, preferred compounds are those where R is straight or branched chain $C_4$–$C_{18}$alkyl or alkenyl, or a mixture thereof, $R_1$ is hydrogen or a moiety $+C_3H_6O)_{\overline{m}}+C_2H_4O)_{\overline{n-1}}CH_2-COO^{\ominus}X^{\oplus}$, m is 0 or an integer 1 to 10, n is an integer 1 to 20, and $x^{\oplus}$ is hydrogen, sodium or lithium. The more preferred compounds of the above formula are those where R is straight or branched chain $C_{10}$–$C_{14}$ alkyl or alkenyl, or a mixture thereof, $R_1$ is a moiety

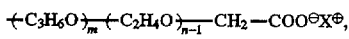

the sum of the m's is 0 or an integer 1 or 2, the sum of the n's is an integer 4 to 10, and $x^{\ominus}$ is hydrogen or sodium.

Suitable alkylpolyglucoside carboxylates which may be prepared by the process of the instant invention include the compounds of formula VIA:

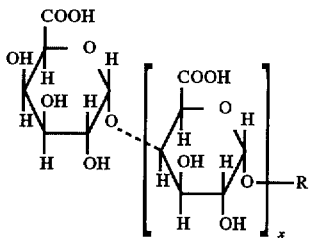

VIA where R is $\underline{n}\text{-}C_1\text{-}C_{25}$alkyl;

and x is 0 or an integer 1 to 100.

Of the compounds of formula VIA, preferred compounds are those where R is $\underline{n}\text{-}C_1\text{-}C_{14}$alkyl, and x is 0 or an integer 1 to 30. The more preferred compounds of formula VIA are those where R is $\underline{n}\text{-}C_1\text{-}C_8$alkyl, and x is 0 or an integer 1 to 15.

Other suitable alkylpolyglucoside carboxylates which may be prepared by the process of the instant invention are the compounds of formula VIB:

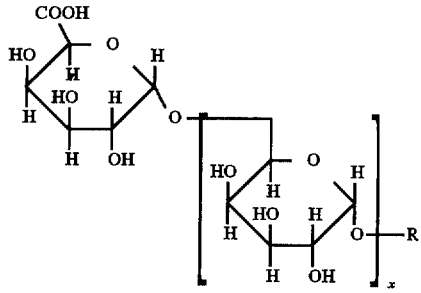

VIB where R is $\underline{n}\text{-}C_1\text{-}C_{25}$alkyl;

and x is 0 to 100.

Of the compounds of formula VIB, preferred compounds are those where R is $\underline{n}\text{-}C_4\text{-}C_{16}$alkyl, and x is 0 to 30. The more preferred compounds of formula VIB are those where R is $\underline{n}\text{-}C_{10}\text{-}C_{13}$-alkyl, and x is 0 to 15.

In accordance with the process of the instant invention, the above-depicted carboxylates are prepared by reacting a primary hydroxyl group-containing polyoxyalkylene compound or alkylpolyglucoside, e.g., a polyoxyalkylene siloxane of the formula

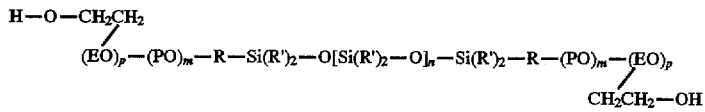

where each R, each R', each m, n and each p are as defined above regarding the compounds of formula IA, or a polyoxyalkylene amine of the formula

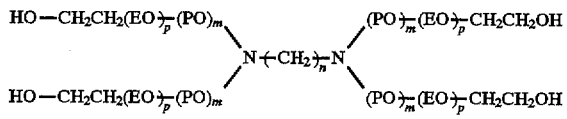

where each m, n and each p are as defined above regarding the compounds of formula IIA, with from 1 to 10 moles of an inorganic or organic halo-containing oxidizing agent in the presence of a weak base and a catalytic amount of a hindered nitroxide compound to produce the desired carboxylates.

As to the oxidizing agent, any inorganic or organic halo-containing oxidizing agent can be utilized in the process of the instant invention. Preferred inorganic halo-containing oxidizing agents are the alkali metal and alkaline earth metal hypochlorites and hypobromites, alkali metal bromites and chlorine gas, whereas preferred organic halo-containing oxidizing agents are trichloroisocyanuric acid, tribromoisocyanuric acid, N-chlorinated and N-brominated succinimides and chlorinated nylon 66. More preferred inorganic halo-containing oxidizing agents are the alkali metal hypochlorites and bromites and chlorine gas, whereas more preferred organic halo-containing oxidizing agents are trichloroisocyanuric acid and chlorinated nylon 66. The oxidizing agent is preferably employed in an amount of from 2 to 6 molar equivalents of the primary hydroxyl group-containing polyoxyalkylene compound or alkylpolyglucoside, more preferably in an amount of from 3 to 4 molar equivalents of the primary hydroxyl group-containing polyoxyalkylene compound or alkylpolyglucoside.

Although any weak base may be employed in the process of the instant invention, the alkali metal bicarbonates are preferred, more preferably sodium and potassium bicarbonate. The weak base is added in an amount sufficient to adjust the pH of the reaction mixture to between 8.0 and 9.0, preferably between 8.5 and 9.0.

With regard to the catalyst, the hindered nitroxide compound (also referred to in the literature as a hindered-iminoxyl or N-oxyl compound) is employed in an amount of from 0.001 to 1 molar equivalents of the primary hydroxyl group-containing polyoxyalkylene compound or alkylpolyglucoside. Preferably, the catalyst is employed in an amount of from 0.01 to 0.10, more preferably 0.02 to 0.04, molar equivalents of the primary hydroxyl group-containing polyoxyalkylene compound or alkylpolyglucoside. The common catalysts are those containing stable nitroxide radicals where geometrical, chemical or sterical factors prevent the formation of a nitrone as depicted below:

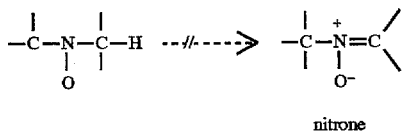

nitrone

The nitroxyl function can be part of a cyclic or acyclic compound, an organic residue, or a polymeric compound. Among the compounds containing stable nitroxide radicals are the hindered nitroxides which may have one, two or several nitroxide containing groups. Such compounds belong, but are not limited, to the following classes of nitroxides:

1) compounds containing one cyclic nitroxide radical, viz., 2,2,6,6 (cis and trans)tetra-substituted piperidine N-oxyl, e.g., 2,2,6,6-tetramethylpiperidine N-oxyl; 2,2,5,5 (cis and trans) tetrasubstituted pyrrolidine N-oxyl, e.g., 2,2,5,5-tetra-methylpyrrolidine N-oxyl; 5,5-dimethyl-2,2-disubstituted pyrrolidine N-oxyl; and (cis trans) 2,5-dimethyl-2,5-disubstituted pyrrolidine-N-oxyl. Other cyclic nitroxides containing one nitroxide radical are: a) 2,2,6,6-tetramethylpiperidine N-oxyl compounds which contain a further substituent in, but not limited to, the 4-position, e.g., 4-acetamido-2,2,6,6-tetramethylpiperidine N-oxyl; 4-phenoxy-2,2,6,6-tetramethyl-piperidine N-oxyl; and compounds of the formula

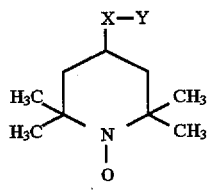

where X is O, N, S, P or C, and Y is a a C—, P—, S—, N— or O— containing group, or X and Y together are part of an organic residue or a polymer; and b) 2,2,5,5-tetra-methylpyrrolidine N-oxyl compounds which contain a further substituent in, but not limited to, the 3-position, e.g., 3-carbamoyl-2,2,5,5-tetra-methylpyrrolidine N-oxyl, 3-cyano-2,2,5,5-tetramethyl-pyrrolidine N-oxyl; and compounds of the formula

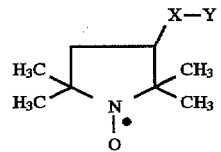

where X and Y are as defined above.

2) compounds containing two cyclic nitroxide radicals, e.g., bis-4,4'-(2,2,6,6-tetra-methylpiperidine N-oxyl) oxamide; bis-3,3'-(2,2,5,5-tetra-methylpyrrolidine N-oxyl) oxamide; and compounds of the formulae

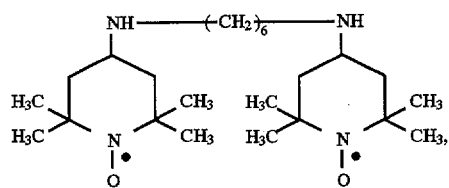

and

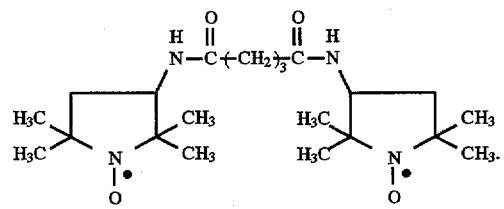

3) compounds containing several cyclic nitroxide radicals, e.g., compounds containing cyclic nitroxide repeating units of the formulae

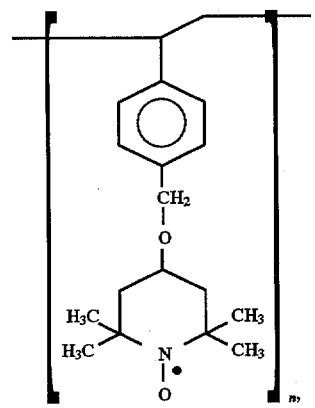

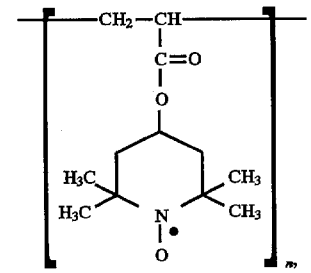

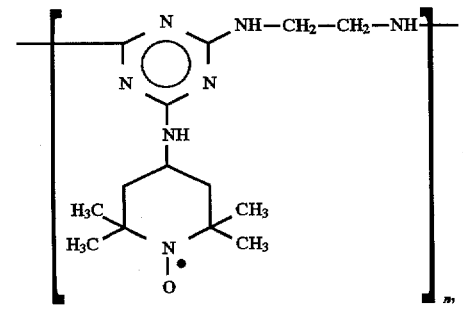

-continued

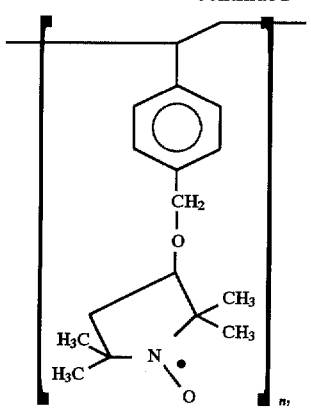

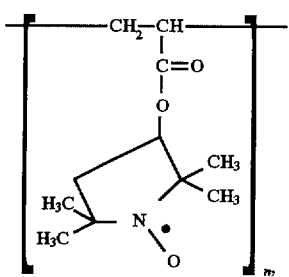

and

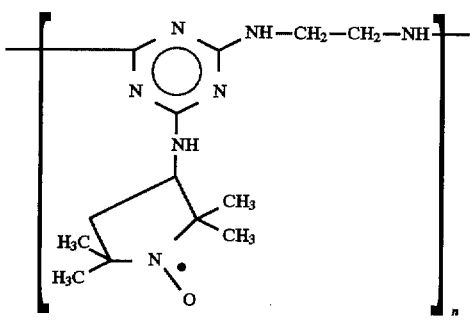

where n is an integer 5 to 5000, preferably 10 to 2000, more preferably 15 to 500.

4) acyclic nitroxides of the formula

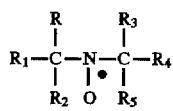

where each of R, $R_1$, $R_2$, $R_3$, $R_4$ and $R_5$ is other than hydrogen, i.e., an alkyl group, an aryl group, etc., e.g., di-t-butylamine N-oxyl, and the compound having the formula

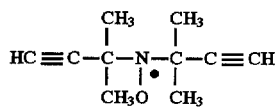

5) acyclic nitroxides of the formula

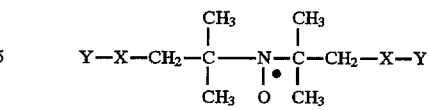

where X and Y are as defined above.

It should be understood that although certain of the moieties represented by the group X-Y in the above compounds are unstable in the reaction mixture, the reaction is not adversely affected since the moieties are away from and, therefore, do not involve the catalytic center. Other suitable catalysts may be employed in the process of the instant invention, e.g., those set forth in "Free Nitroxyl Radicals" by E.G. Rozantsev, Plenum Press. New York; London (1970), "Organic Chemistry of Stable Free Radicals" by A. R. Forrester, et al., Academic Press London and New York (1968), "Spin Labeling in Pharmacology", J. L. Holtzman, Academic Press (1984), and Chemicals Review, Vol. 78(1), pgs. 37–64(1978). Moreover, the macrocyclic molecules described in U.S. Pat. No. 4,442,250 and U.S. Pat. No. 4,780,493 can be oxidized to the corresponding N-oxyl derivatives and utilized as catalysts in the process of the instant invention. In addition, it should be made understood that a mixture of hindered nitroxide compounds may be employed as the catalyst in the process of the instant invention and such catalyst mixtures are intended to be included within the scope of the instant invention.

The preparation of the carboxylates is conducted at a temperature of from −10° to 50° C., preferably between −5° and 40° C., more preferably between 10° and 30° C.

As to reaction times, the rate of addition of the oxidizing agent determines the duration of the reaction. Thus, the addition of the oxidizing agent is at a rate such that the oxidizing agent does not accumulate in the reaction mixture. Generally, the oxidizing agent is added over a period of 2 to 3 hours, after which time the reaction mixture is allowed to react for an additional 30 to 60 minutes. Therefore, the total reaction time is at least 3 hours, preferably between 3 and 4 hours.

It should be understood that the resultant carboxylates may possess varying levels of carboxylation depending on the stoichiometry of the reaction. Thus, the ratio [mole of starting material]/[mole of carboxylate] can be tuned to a preset level, depending upon the amount of oxidizing agent employed, i.e., the level of carboxylation is a function of the level of oxidizing agent.

The primary hydroxyl group-containing polyoxyalkylene siloxanes employed in preparing the carboxylates of formula IA are commercially available from Genesee Polymers Corporation and from Petrarch System whereas the corresponding siloxanes employed in preparing the carboxylates of formula IB are commercially available from Union Carbide. In addition, the primary hydroxyl group-containing polyoxyalkylene amines employed in preparing the carboxylates of formula IIA are commercially available from BASF; the corresponding amines employed in preparing the carboxylates of formula IIB are commercially available from Sandoz Chemicals Corp.; and the corresponding amines employed in preparing the carboxylates of formula IIC are commercially available from Akzo Chemicals. Analogously, the corresponding amines employed in preparing the carboxylates of formulae IID, IIE and IIF, the alkylpolyoxyalkylene alcohols employed in preparing the carboxylates of formula III, the polyoxyalkylene block polymers employed in preparing the carboxylates of formula IV, the alkylamidepolyoxyalkylenes employed in preparing the carboxylates of formula V, and the alkyl polyglucosides employed in preparing the carboxylates of formulae VIA and VIB are either known and obtained by methods described in the literature, or where not known, may be obtained by methods analogous to those described in the literature.

Although many of the carboxylates prepared by the process of the instant invention are known, the polyoxyalkylene amine and alkylamidepolyoxyalkylene carboxylates are novel compounds and, as such, they represent another aspect of the instant invention.

The following examples are for the purposes of illustration only and are not intended in any way to limit the scope of the instant invention.

EXAMPLE 1

Preparation of polyoxyalkylene siloxane carboxylate of formula IA (R is propyl; R' is methyl; m is 0, n is 4 and p is 27):
Process A: (employing a liquid oxidizing agent)

To a 1000 ml beaker equipped with an overhead stirrer is added 91.35 g of PS-556 (a carbinol terminated polydimethylsiloxane having a molecular weight of 1000 and available commercially from Petrarch System, Bristol, Pa.), 12.5 g of sodium bicarbonate and 1.14 g of Tempo (2,2,6,6-tetramethylpiperidine N-oxyl). To the stirred reaction mixture is added, portionwise over a period of 3 hours, 385 ml of a 1.91M aqueous sodium hypochlorite solution (freshly prepared, protected against light by an aluminum foil wrap, and adjusted to a pH of 8.6 by the addition of sodium bicarbonate). The resultant reaction mixture is stirred for an additional hour and sodium bisulfite is added to get a negative reading in the starch-iodide test. The reaction mixture is then concentrated by ultrafiltration to obtain the desired carboxylate in sodium salt form.

Process B: (employing a solid or gaseous oxidizing agent)

To a 2000 ml beaker equipped with an overhead stirrer is added 500 ml of distilled water and 1.14 g of Tempo. With stirring, 91.35 g of PS-556 is dissolved in the aqueous solution and the pH of the resultant solution is adjusted to 8.6 by the addition of sodium bicarbonate. To the stirred mixture is added, portionwise at 30 minute intervals over a period of 3 hours, 156 g of calcium hypochlorite (67.2%), and the pH is adjusted to 8.6, if necessary, by the addition of sodium bicarbonate every time a portion of calcium hypochlorite is added. The resultant reaction mixture is stirred for an additional hour and sodium bisulfite is added to get a negative reading in the starch-iodide test. The reaction mixture is then concentrated to obtain the desired carboxylate in sodium salt form.

EXAMPLE 2

Preparation of polyoxyalkylene amine carboxylate of formula IIA (the sum of the m's is ~16; n is 2; and the sum of the p+s is ~12, calculated by disregarding the ethylene diamine contribution)
Process A (employing a liquid oxidizing agent)

To a 1000 ml beaker equipped with an overhead stirrer is added 103 g of Tetronic-304 (an ethylene diamine based polyoxyalkylene amine having a molecular weight of 1650 and available commercially from BASF), 12.5 g of sodium bicarbonate and 1.56 g of Tempo. To the stirred reaction mixture is added, portionwise over a period of 3 hours, 525 ml of a 1.91M aqueous sodium hypochlorite solution (freshly prepared, protected against light by an aluminum foil wrap and adjusted to a pH of 8.6 by the addition of sodium bicarbonate). The resultant reaction mixture is stirred for an additional hour and acidified to a pH of between 2 and 3 with hydrochloric acid. The acidic reaction mixture is then heated to the cloud point and the organic upper layer is separated from the aqueous phase to obtain the desired carboxylate as an oily liquid.

Process B (employing a solid or gaseous oxidizing agent)

To a 2000 ml beaker equipped with an overhead stirrer is added 500 ml of distilled water and 1.56 g of Tempo. With stirring, 103 g of Tetronic-304 is dissolved in the aqueous solution and the pH of the resultant solution is adjusted to 8.6 by the addition of sodium bicarbonate. To the stirred mixture is added, portionwise at 30 minute intervals over a period of 3 hours, 213 g of calcium hypochlorite (67.2%), and the pH is adjusted to 8.6, if necessary, by the addition of sodium bicarbonate every time a portion of calcium hypochlorite is added. The resultant reaction mixture is stirred for an additional hour and acidified to a pH of between 2 and 3 with hydrochloric acid. The acidic reaction mixture is then heated to the cloud point and the organic upper layer is separated from the aqueous phase to obtain the desired carboxylate as an oily liquid.

EXAMPLE 3

Preparation of polyoxyalkylene amine carboxylate of formula IIC (m is 0; the sum of the p+s is 13 and x is an average value of between 10 and 12)
Process A (employing a liquid oxidizing agent)

To a 1000 ml beaker equipped with an overhead stirrer is added 100 g of Ethomeen C/25 (a fatty amine based polyoxyalkylene amine having a molecular weight of 860 and available commercially from Akzo Chemicals, Inc.), 12.5 g of sodium bicarbonate and 1.45 g of Tempo. To the stirred reaction mixture is added, portionwise over a period of 3 hours, 490 ml of a 1.91M aqueous sodium hypochlorite solution (freshly prepared, protected against light by an aluminum foil wrap and ajusted to a pH of 8.6 by the addition of sodium bicarbonate). The resultant reaction mixture is stirred for an additional hour and acidified to a pH of between 2 and 3 with hydrochloric acid. The acidic reaction mixture is then heated to the cloud point and the organic upper layer is separated from the aqueous phase to obtain the desired carboxylate as an oily liquid.

Process B (employing a solid or gaseous oxidizing agent)

To a 2000 ml beaker equipped with an overhead stirrer is added 500 ml of distilled water and 1.45 g of Tempo. With stirring, 100 g of Ethomeen C/25 is dissolved in the aqueous solution and the pH of the resultant solution is adjusted to 8.6 by the addition of sodium bicarbonate. To the stirred mixture is added, portionwise at 30 minute intervals over a period of 3 hours, 198 g of calcium hypochlorite (67.2%) and the pH is adjusted to 8.6, if necessary, by the addition of sodium bicarbonate every time a portion of calcium hypochlorite is added. The resultant reaction mixture is stirred for an additional hour and acidified to a pH of between 2 and 3 with hydrochloric acid. The acidic reaction mixture is then heated to the cloud point and the organic upper layer is separated from the aqueous phase to obtain the desired carboxylate as an oily liquid.

EXAMPLE 4

Preparation of polyoxyalkylene amine carboxylate of formula IIF (R is methyl; m is 0; the sum of the p's is 13; x is 12 to 14; and $X^{\ominus}$ is chloride):
Process A (employing a liquid oxidizing agent)

To a 1000 ml beaker equipped with an overhead stirrer is added 100 g of Ethoquad C/25 (a dialkylamine based polyoxyalkylene quaternary amine having a molecular weight of 925 and available commercially from Akzo Chemicals, Inc.), 30 g of sodium bicarbonate and 1.35 g of Tempo. To the stirred reaction mixture is added, portionwise over a period of 3 hours, 455 ml of a 1.91M aqueous sodium hypochlorite solution (freshly prepared, protected against light by an aluminum foil wrap and adjusted to a pH of 8.6 by the addition of sodium bicarbonate). The resultant reaction mixture is stirred for an additional hour and concentrated by nanofiltration. The resultant viscous liquid is then acidified to a pH of between 2 and 3 with hydrochloric acid to obtain the desired carboxylate.

Process B (employing a solid or gaseous oxidizing agent)

To a 2000 ml beaker equipped with an overhead stirrer is added 500 ml of distilled water and 1.35 g of Tempo. With stirring, 100 g of Ethoquad C/25 is dissolved in the aqueous solution and the pH of the resultant solution is adjusted to 8.6 by the addition of sodium bicarbonate. To the stirred mixture is added, portionwise at 30 minute intervals over a period of 3 hours, 185 g of calcium hypochlorite (67.2%) and the pH is adjusted to 8.6, if necessary, by the addition of sodium bicarbonate every time a portion of calcium hypochlorite is added. The resultant reaction mixture is stirred for an additional hour and concentrated by nanofiltration. The resultant viscous liquid is then acidified to a pH of between 2 and 3 with hydrochloric acid to obtain the desired carboxylate.

EXAMPLE 5

Preparation of alkylpolyoxyalkylene carboxylate of formula III (R is the residue of a mixture of $C_{10}$–$C_{14}$ straight chain alcohols; m is 0 and n is 6)

Process A (employing a liquid oxidizing agent and a cyclic nitroxide containing two nitroxide radicals as catalyst)

a) Preparation of bis-4,4'-(2,2,6,6-tetramethyl-piperidine) oxamide.

To a three-neck flask equipped with a thermometer, a mechanical stirrer, a condenser and a dropping funnel is added 300 ml of ethanol, 300 ml of toluene, 150 g (1 mole) of 4-amino-2,2,6,6-tetramethylpiperidine and 73 g (0.5 moles) of diethyloxalate. The resultant mixture is then refluxed for 10 hours and cooled to room temperature. The resultant white solid is then collected by filtration and dried in vacuo to obtain the desired compound.

b) Preparation of bis-4,4'-(2,2,6,6-tetramethyl-piperidine N-oxyl)oxamide.

In accordance with a modification of the procedure set forth by M. G. Rosen, et al. in Synthetic Communications, Vol. 5 (6), pgs. 409–413 (1975), the compound prepared in a) above, was oxidized as follows:

To a three-neck flash stirrer is added overhead stirrer is added 36.6 g (0.1 moles) of the compound prepared in a) above, 250 ml of methanol, 100 ml of acetonitrile, 14 g of sodium bicarbonate and 5 g (0.015 moles) of sodium tungstate dihydrate. After cooling the resultant mixture on an ice bath, 250 ml of hydrogen peroxide (30% soln.) was added to the mixture and, after removing the ice bath, the reaction mixture was stirred at room temperature for 3 days. The reaction mixture was then again cooled on an ice bath, an additional 250 ml of hydrogen peroxide (30% soln.) was added to the mixture and, after removing the ice bath, the reaction mixture was stirred at room temperature for 5 days. The reaction mixture was then transferred to a beaker containing 600 g of crushed ice, after which time the resultant mixture was triturated and allowed to warm to room temperature. After filtration, the resultant crystals were dried overnight at 80° C. to obtain the desired compound.

Preparation of the title compound

To a 1000 ml beaker equipped with an overhead stirrer is added 127.5 g of Tergitol 24L-60N (a polyoxyalkylene alcohol having a molecular weight of 510 and available commercially from Union Carbide), 750 ml of water, 31 g of sodium bicarbonate and 20 g of the compound prepared in b) above. To the stirred reaction mixture is added, portionwise over a period of 3 hours, 525 ml of a 1.91M aqueous sodium hypochlorite solution (freshly prepared, protected against light by an aluminum foil wrap and adjusted to a pH of 8.6 by the addition of sodium bicarbonate). The resultant reaction mixture is stirred for an additional hour and filtered to recover the catalyst which can be reused without reactivation. The resultant filtrate is then acidified to a pH of between 2 and 3 with hydrochloric acid. The acidic reaction mixture is then heated to the cloud point and the organic upper layer is separated from the aqueous phase to obtain the desired carboxylate as an oily liquid.

Process B (employing a gaseous oxidizing agent)

A 1000 ml reactor is equipped with an overhead stirrer, a thermometer, a pH electrode, and a chlorine-disperser for subsurface addition. The pH electrode is connected to an ACUMET pH-meter for monitoring automatically the pH and adjusting it to a pre-set value of 8.6 by adding a 50% solution of sodium hydroxide. To the reactor is added 600 ml of distilled water, 3.14 g of Tempo and 22 g of sodium bicarbonate. With stirring, 255 g of Tergitol 24L-60N is dissolved in the aqueous solution and the pH of the resultant solution is adjusted to 8.6 by the addition of sodium bicarbonate. A slow but continuous stream of chlorine is then bubbled into the stirred reaction mixture over a period of 3 hours, while the temperature is maintained at 25° C. The flow of chlorine is then stopped and the resultant reaction mixture is stirred for an additional hour. The ACUMET automatic dispenser is then disconnected while a flow of chlorine is bubbled into the rection mixture to lower the pH to 2. The acidic reaction mixture is then heated to its cloud point and the organic upper layer is separated from the aqueous phase to obtain the desired carboxylate as a colorless to slightly brown oily liquid.

EXAMPLE 6

Preparation of polyoxyalkylene block polymer carboxylate of formula IV (m+p is ~8, and n is ~22)

Process A (employing a liquid oxidizing agent and a cyclic nitroxide containing several nitroxide radicals as catalyst)

a) Preparation* of polyvinylbenzyl-4—O—2,2,6,6-tetramethylpiperidine N-oxyl

To a flame-dried, three-neck flask equipped with a nitrogen inlet-outlet and a magnetic stirring bar is added 5 g of 4-hydroxy-2,2,6,6-tetramethylpiperidine N-oxyl and 200 ml of anhydrous dimethylformanide. To the mixture is added, portionwise and under a flow of nitrogen, 2 g of sodium hydride and the resultant mixture is stirred at room temperature for 45 minutes. 10 g of polyvinylbenzyl chloride is then added, portionwise, and the resultant mixture is stirred at room temperature for 10 hours. The reaction mixture is then drowned in 1 liter of icy-cold water and the resultant pink precipitate is isolated by filtration and dried in vacuo overnight to obtain the desired compound.

Preparation of the title compound

To a 1000 ml beaker equipped with an overhead stirrer is added 120 g of Pluronic L-42 (a polyoxyalkylene-polyoxyalkylene block polymer having a molecular weight of 1630 and available commercially from BASF), 12.5 g of sodium bicarbonate and 10 g of the compound prepared in a) above. To the stirred reaction mixture is added, portionwise over a period of 3 hours, 310 ml of a 1.91M aqueous sodium hypochlorite solution (freshly prepared, protected against light by an aluminum foil wrap and adjusted to a pH of 8.6 by the addition of sodium bicarbonate). The resultant reaction mixture is stirred for an additional hour and filtered to recover the catalyst which can be reused without reactivation. The resultant filtrate is then acicified to a pH of between 2 and 3 with hydrochloric acid. The acidic reaction mixture is then heated to the cloud point and the organic upper layer is separated from the aqueous phase to obtain the desired carboxylate as an oily liquid.

Process B (employing a solid or gaseous oxidizing agent)

To a 2000 ml beaker equipped with an overhead stirrer is added 500 ml of distilled water and 0.92 g of Tempo. With stirring, 120 g of Pluronic L-42 is dissolved in the aqueous solution and the pH of the resultant solution is adjusted to 8.6 by the addition of sodium bicarbonate. To the stirred mixture is added, portionwise at 30 minute intervals over a period of 3 hours, 125.33 g of calcium hypochlorite (67.2%) and the pH is adjusted to 8.6, if necessary, by the addition of sodium bicarbonate every time a portion of calcium hypochlorite is added. The resultant reaction mixture is stirred for an additional hour and acidified to a pH of between 2 and 3 with hydrochloric acid. The acidic reaction mixture is then heated to the cloud point and the organic upper layer is separated from the aqueous phase to obtain the desired carboxylate as an oily liquid.

EXAMPLE 7

Preparation of alkylamidepolyoxyalkylene carboxylate of formula V (R is the residue of a mixture of $C_{10}$–$C_{12}$ straight chain alcohols; $R_1$ is a moiety $-(C_2H_4O)_{n-1}CH_2-COO^{\ominus}X^{\oplus}$; m is 0 and the sum of the n's is 7)

Process A (employing a liquid oxidizing agent)

To a 1000 ml beaker equipped with an overhead stirrer is added 100 g of Alkamidox C-5 (an alkylamidepolyoxyalkylene having a molecular weight of 521 and available commercially from Alkaril Chemical), 12.5 g of sodium bicarbonate and 2.4 g of Tempo. To the stirred reaction mixture is added, portionwise over a period of 3 hours, 804 ml of a 1.91M aqueous sodium hypochlorite solution (freshly prepared, protected against light by an aluminum foil wrap and adjusted to a pH of 8.6 by the addition of sodium bicarbonate). The resultant reaction mixture is stirred for an additional hour and acidified to a pH of between 2 and 3 with hydrochloric acid. The acidic reaction mixture is then heated to the cloud point and the organic upper layer is separated from the aqueous phase to obtain the desired carboxylate as on oily liquid.

Process B (employing a solid or gaseous oxidizing agent)

To a 2000 ml beaker equipped with an overhead stirrer is added 500 ml of distilled water and 2.4 g of Tempo. With stirring, 100 g of Alkamidox C-5 is dissolved in the aqueous solution and the pH of the resultant solution is adjusted to 8.6 by the addition of sodium bicarbonate. To the stirred mixture is added, portionwise at 30 minute intervals over a period of 3 hours, 327 g of calcium hypochlorite (67.2%) and the pH is adjusted to 8.6, if necessary, by the addition of sodium bicarbonate every time a portion of calcium hypochlorite is added. The resultant reaction mixture is stirred for an additional hour and acidified to a pH of between 2 and 3 with hydrochloric acid. The acidic reaction mixture is then heated to the cloud point and the organic upper layer is separated from the aqueous phase to obtain the desired carboxylate as an oily liquid.

EXAMPLE 8

Preparation of alkylpolyglucoside carboxylate of formula VIB (R is $C_{10}$–$C_{13}$ and x is 0.6):

Process A (employing a liquid oxidizing agent)

To a 1000 ml beaker equipped with an overhead stirrer is added 100 g of APG-625 (an alkylpolyglucoside having a molecular weight of 429 and available commercially from Henkel Corporation as a 50% dispersion in water), 30 g of sodium bicarbonate and 1.46 g of Tempo. To the stirred reaction mixture is added, portionwise over a period of 3 hours, 490 ml of a 1.91M aqueous sodium hypochlorite solution (freshly prepared, protected against light by an aluminum foil wrap and adjusted to a pH of 8.6 by the addition of sodium bicarbonate). The resultant reaction mixture is stirred for an additional hour, after which time it is concentrated by nanofiltration to obtain the desired carboxylate as a viscous liquid.

Process B (employing a solid or gaseous oxidizing agent)

To a 2000 ml beaker equipped with an overhead stirrer is added 500 ml of distilled water and 1.46 g of Tempo. With stirring, 200 g of APG-625 is dissolved in the aqueous solution and the pH of the resultant solution is adjusted to 8.6 by the addition of sodium bicarbonate. To the stirred mixture is added, portionwise at 30 minute intervals over a period of 3 hours, 200 g of calcium hypochlorite (67.2%) and the pH is adjusted to 8.6, if necessary, by the addition of sodium bicarbonate every time a portion of calcium hypochlorite is added. The resultant reaction mixture is stirred for an additional hour after which time it is concentrated by nanofiltration to obtain the desired carboxylate as a viscous liquid.

What is claimed is:

1. A process for preparing a polyoxyalkylene siloxane carboxylate comprising reacting a primary hydroxyl group-containing polyoxyalkylene siloxane with at least an equimolar amount of either an inorganic or organic halo-containing oxidizing agent in the presence of a weak base and a catalytic amount of a hindered nitroxide.

2. A process according to claim 1 wherein the oxidizing agent is present in an amount of from 1 to 10 molar equivalents of the primary hydroxyl group-containing polyoxyalkylene siloxane.

3. A process according to claim 2 wherein the oxidizing agent is present in an amount of from 2 to 6 molar equivalents of the primary hydroxyl group-containing polyoxyalkylene siloxane.

4. A process according to claim 3 wherein the oxidizing agent is present in an amount of from 3 to 4 molar equivalents of the primary hydroxyl group-containing polyoxyalkylene siloxane.

5. A process according to claim 1 wherein the hindered nitroxide is selected from the group consisting of compounds containing one cyclic nitroxide radical, two cyclic nitroxide radicals and several cyclic nitroxide radicals, and acyclic nitroxides.

6. A process according to claim 1 comprising reacting the primary hydroxy group-containing polyoxyalkylene siloxane with from 1 to 10 molar equivalents of an alkali metal hypochlorite in the presence of an alkali metal bicarbonate and from 0.001 to 1 molar equivalents of a hindered nitroxide at a temperature of from −10° to 50° C.

7. A process according to claim 6 comprising reacting the primary hydroxyl group-containing polyoxyalkylene siloxane with from 2 to 6 molar equivalents of an alkali metal hypochlorite in the present of an alkali metal bicarbonate and from 0.01 to 0.10 molar equivalents of a hindered nitroxide at a temperature of from −5° to 40° C.

8. A process according to claim 7 comprising reacting the primary hydroxyl group-containing polyoxyalkylene siloxane with from 3 to 4 molar equivalents of an alkali metal hypochlorite in the presence of an alkali metal bicarbonate and from 0.02 to 0.04 molar equivalents of a hindered nitroxide at a temperature of from 10° to 30° C.

9. A process according to claim 1 wherein the oxidizing agent is selected from alkali metal hypochlorites, alkali metal bromites and chlorine gas.

10. A process according to claim 9 wherein the oxidizing agent is an alkali metal hypochlorite.

11. A process according to claim 10 wherein the oxidizing agent is sodium hypochlorite.

12. A process according to claim 1 wherein the oxidizing agent is selected from trichloroisocyanuric acid and chlorinated nylon 66.

13. A process according to claim 1 wherein the weak base is an alkali metal bicarbonate.

14. A process according to claim 13 wherein the weak base is sodium bicarbonate.

15. A process according to claim 5 wherein the hindered nitroxide is a compound containing one cyclic nitroxide radical selected from the group consisting of 2,2,6,6-tetramethylpiperidine N-oxyl, 2,2,5,5-tetramethylpyrrolidine N-oxyl, 4-acetamido-2,2,6,6-tetramethylpiperidine N-oxyl, 4-phenoxy-2,2,6,6-tetramethyl-piperidine N-oxyl, 3-carbamoyl-2,2,5,5-tetramethylpyrrolidine N-oxyl and 3-cyano-2,2,5,5-tetramethylpyrrolidine N-oxyl.

16. A process according to claim 15 wherein the hindered nitroxide is 2,2,6,6-tetramethylpiperidine-N-oxyl.

17. A process according to claim 5 wherein the hindered nitroxide is a compound containing two cyclic nitroxide radicals selected from the group consisting of bis-4,4'-(2,2,6,6-tetramethylpiperidine N-oxyl)oxamide, bis-3,3'-(2,2,5,5-tetramethylpyrrolidine N-oxyl)oxamide, the compound of the formula

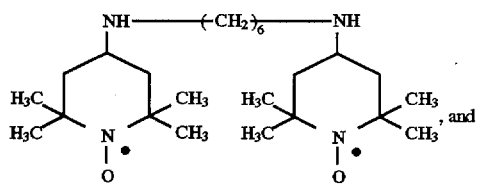

the compound of the formula

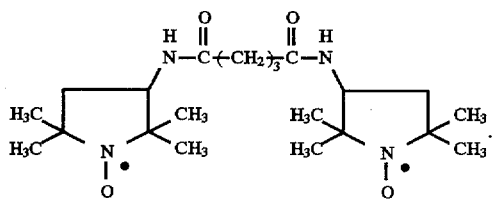

18. A process according to claim 17 wherein the hindered nitroxide is bis-4,4'-(2,2,6,6-tetramethylpiperidine N-oxyl) oxamide.

19. A process according to claim 5 wherein the hindered nitroxide is a compound containing several cyclic nitroxide radicals selected from the group consisting of

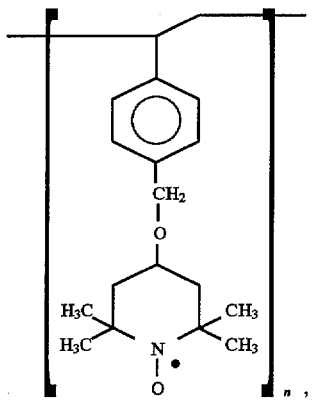

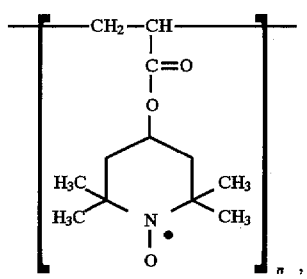

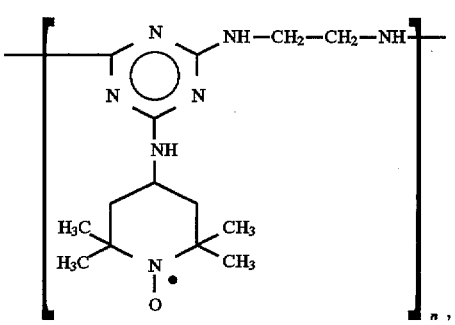

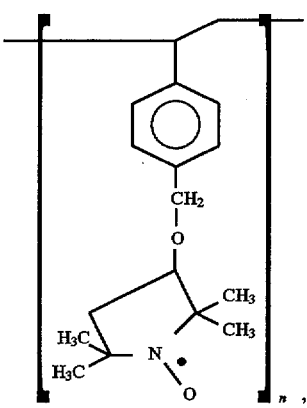

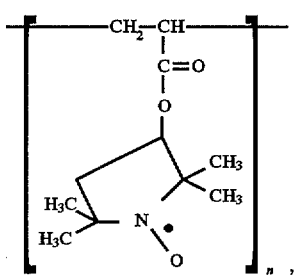

-continued and

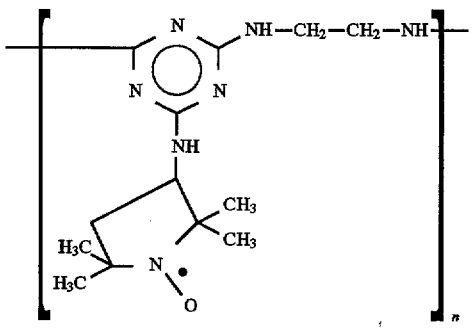

where n is an integer 5 to 5000.

20. A process according to claim 19 wherein the hindered nitroxide is a compound having the formula

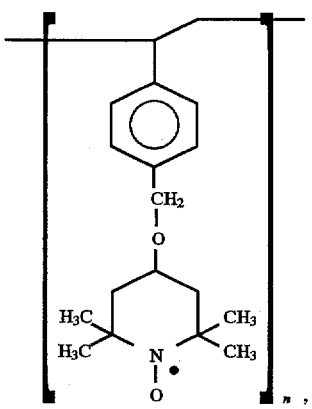

where n is as defined in claim 19.

21. A process according to claim 5 wherein the hindered nitroxide is an acyclic nitroxide selected from di-t-butylamine N-oxyl and the compound having the formula

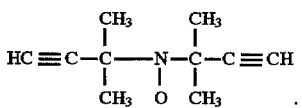

22. A process according to claim 1 wherein the hindered nitroxide is employed in an amount of from 0.001 to 1 molar equivalents of the primary hydroxyl group-containing polyoxyalkylene siloxane.

23. A process according to claim 22 wherein the hindered nitroxide is employed in an amount of from 0.01 to 0.10 molar equivalents of the primary hydroxyl group-containing polyoxyalkylene siloxane.

24. A process according to claim 23 wherein the hindered nitroxide is employed in an amount of from 0.02 to 0.04 molar equivalents of the primary hydroxyl group-containing polyalkylene siloxane.

25. A process according to claim 1 wherein the reaction is conducted at a temperature of from $-10°$ to $50°$ C.

26. A process according to claim 25 wherein the reaction is conducted at a temperature of from $-5°$ to $40°$ C.

27. A process according to claim 26 wherein the reaction is conducted at a temperature of from $10°$ to $30°$ C.

28. A process according to claim 1 wherein the polyoxyalkylene siloxane carboxylate is a compound of formula IB:

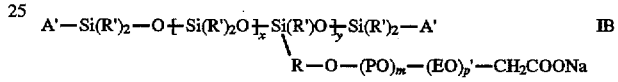    IB where R is $C_1$–$C_{20}$alkyl;

each R' is $C_1$–$C_{20}$alkyl, aryl or benzyl;

m is 0 or an integer 1 to 100;

p' is an integer 1 to 200;

each A' has the same significance as R' defined above or is a group where R, m and p are as defined above; and x+y is 0 or an integer 1 to 1000.

29. A process according to claim 8 wherein the alkali metal hypochlorite is sodium hypochlorite.

30. A process according to claim 8 wherein the reaction is conducted in the presence of sodium bicarbonate.

31. A process according to claim 8 wherein the reaction is conducted at a pH of from 8.0 to 9.0.

32. A process according to claim 8 wherein the reaction is conducted at a pH of from 8.5 to 9.0.

* * * * *